(12) United States Patent
Schaffner et al.

(10) Patent No.: US 8,323,672 B2
(45) Date of Patent: *Dec. 4, 2012

(54) METHOD OF REMOVING TICKS FROM THE SKIN AND REDUCING THE RISK OF BITES

(75) Inventors: Carl P. Schaffner, Hamilton, NJ (US); William K. Griesinger, Ringoes, NJ (US)

(73) Assignee: Karykion Corporation, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,811

(22) Filed: Jul. 7, 2011

(65) Prior Publication Data

US 2012/0003333 A1    Jan. 5, 2012

Related U.S. Application Data

(63) Continuation-in-part of application No. 12/498,971, filed on Jul. 7, 2009, now abandoned, which is a continuation of application No. 11/512,555, filed on Aug. 29, 2006, now Pat. No. 7,604,814.

(51) Int. Cl.
*A01N 25/02* (2006.01)
*A01N 39/02* (2006.01)

(52) U.S. Cl. ........ 424/405; 424/406; 424/769; 514/159; 514/557

(58) Field of Classification Search .................. None
See application file for complete search history.

(56) References Cited

U.S. PATENT DOCUMENTS

| | | | |
|---|---|---|---|
| 4,668,434 | A | 5/1987 | Bowman |
| 5,756,118 | A | 5/1998 | Deckner et al. |
| 6,683,065 | B1 | 1/2004 | Holzer |
| 6,808,717 | B1 | 10/2004 | Bale |
| 7,604,814 | B2 | 10/2009 | Schaffner et al. |
| 2004/0157766 | A1 | 8/2004 | Embil et al. |
| 2006/0008538 | A1 | 1/2006 | Wu et al. |
| 2006/0153935 | A1 | 7/2006 | Blahut |
| 2006/0275218 | A1 | 12/2006 | Tamarkin et al. |

OTHER PUBLICATIONS

Hauser, S. C., "Outwitting Ticks: The Prevention and Treatment of Lyme Disease and Ailments Caused by Ticks, Scorpions, Spiders, and Mites", First Edition, 2001, pp. 63-66 and 99-101, The Lyons Press, USA.

*Primary Examiner* — Neil Levy
(74) *Attorney, Agent, or Firm* — Edward S. Wright

(57) ABSTRACT

Compositions and method of using the same for the removal of ticks embedded in the skin or tissue of a human or animal host and for preventing ticks from attaching themselves to and biting humans or other animals.

16 Claims, No Drawings

METHOD OF REMOVING TICKS FROM THE SKIN AND REDUCING THE RISK OF BITES

RELATED APPLICATIONS

Continuation-in-part of Ser. No. 12/498,971, filed Jul. 7, 2009, abandoned, which was a continuation of Ser. No. 11/512,555, filed Aug. 29, 2006, now U.S. Pat. No. 7,604,814, issued Oct. 20, 2009, the priorities of which are claimed.

BACKGROUND OF THE INVENTION

1. Field of Invention

This invention relates to compositions, articles containing compositions, and methods of use of the compositions, for rapid and efficacious removal of ticks (Arthropods) attached to a mammal.

2. Related Art

Ticks have life cycles starting with eggs produced by adult females. These hatch and progress to larvae, nymphs, and adults. With Lyme disease, the bite of the nymph offers the greatest risks to humans and animals and that of the adult less so. The disease causing pathogen of Lyme disease is found in the gut of the blacklegged ticks where it remains inactive until warm blood enters the gut and enables it to grow and then move to the mouth of the tick. This process takes anywhere from 24 to 36 hours. Other tick-borne disease pathogens have even shorter growth periods. The soft-shelled tick, *Ornithodoros hermsi* that causes Relapsing Fever requires only one hour or less to be available for infection at the bite site. Hauser, Susan Carol, 2001, in "Outwitting Ticks", The Lyons Press, Connecticut, presents an extensive survey of the role of ticks in human and animal diseases, their description, location, prevention and treatment. The conclusion of this author and all health authorities is that embedded ticks of all types should be removed as quickly as possible. In the case of Lyme disease the tick should be removed before 24 hours after the time of attachment. This process is not always so simple.

Various household methods currently attempt to remove ticks ranging from applying heat or various chemical compositions. However, these household remedies may not be safe due to the potential danger of burning skin when applying heat or because many of the chemicals can be unhealthy and adversely react with human skin causing irritations or rashes.

Others have attempted to create less dangerous methods for removing ticks. For example Bale, U.S. Pat. No. 6,808,717 discloses an aerosol coolant spray for killing and removing ticks comprising a coolant spray and essential oil. However, using aerosol canisters are undesirable due to the release of volatile organic compounds (VOCs) into the atmosphere that may cause pollution and depletion of the Earth's ozone layer. Other alternatives include using specially formulated shampoos that are safer for human and animal use such as those disclosed in Holzer, U.S. Pat. No. 6,683,065 and Bowman, U.S. Pat. No. 4,668,434. However, these methods may not be as effective at removing ticks due to the dilution of the effective chemicals.

OBJECTS AND SUMMARY OF THE INVENTION

It is, in general, an object of the invention to provide a new and improved composition and method for removing ticks from the skin of subjects such as humans and other animals and reducing the risk of tick bites.

Another object of the invention is to provide a composition and method of the above character which overcome the limitations and disadvantages of methods heretofore employed in the removal of ticks.

These and other objects are achieved in accordance with the invention by applying a composition containing salicylic acid and an astringent to a tick and/or to a subject near the tick in an amount sufficient to disengage the tick from the subject. The salicylic acid and the astringent are applied in amounts sufficient to render ineffective cementitious substances secreted by ticks to attach themselves to the skin and to constrict blood vessels near the skin and thereby keep blood away from the skin where ticks might feed upon it. In some embodiments, the composition is applied to the skin before a tick has attached itself to a subject to prevent ticks from attaching themselves to and biting the subject.

DETAILED DESCRIPTION

Unless defined otherwise, all technical and scientific terms used herein have the same meaning as is commonly understood by one of skill in the art to which this invention belongs. All publications and patents referred to herein are incorporated by reference.

Tick insects are arthropods related to spiders, mites and fleas. There are a variety of ticks found throughout the world and they are dependent on animal and human hosts for survival. They are also excellent hosts in turn to many microbial pathogens including bacteria and viruses that are responsible for many diseases of humans and animals.

In the United States Lyme disease now account for more than 95 percent of all reported tick vector borne illnesses. In endemic areas 3 percent or more of the population experience the disease. Between 1982 and 2001 there has been a 25 fold increase in the incidence of Lyme disease in humans and the rate of disease progression and geographical area are increasing.

Lyme disease is caused by the bacterium *Borrelia burgdorferi* that is carried and supported by the black-legged tick, *Ixodes scapularis*, in Eastern and upper Midwestern United States. On the West Coast of the United States the black-legged tick, *Ixodes pacificus* is involved in the cause of Lyme disease. In Europe and Asia the blacklegged ticks that serve as host carriers for *Borrelia burgdorferi* and cause Lyme disease are *Ixodes ricinus* and *Ixodes persulcatus*, respectively. Lyme disease is a multisystem infection caused generally by the bacterium, *Borrelia burgdorferi*, a spirochete that can infect both humans and different animals.

Another spirochete that causes the disease, syphilis, does not require a tick transmission host but infects human to human. Lyme disease has a well-established infection pathway involving compatible host reservoirs such as mice and deer. As an essential vector blacklegged ticks transport the infectious bacterium from mice to humans.

In the United States there are other tick-borne diseases of considerable importance to human health. Rocky Mountain Spotted Fever caused by *Rickettsia rickittsi* is hosted and transmitted by the tick, *Dermacentor variabilis*, found in the East and South of the United States while in the West the tick, *Dermacentor Andersen*, is involved in infection and transmission. A more recent disease, Babesiosis, caused by *Babesia microti* is hosted by the blacklegged tick, *Ixodes scapularis* and found in the Northeast while on the West coast the tick, *Ixodes pacificus*, transmits the bacterium, *Babesia equi*. The disease can be cotransmitted with Lyme disease and resembles malaria since the microbe invades red blood cells.

A more recently identified tick related disease called Erhlichiosis is caused by rickettsial bacteria. There are two distinct forms of the disease. One form known as monocytic ehrlichiosis (HME) is caused by the rickettsial bacterium, *Ehrlichia chaffeensis* and is hosted and transmitted by the ticks, *Dermacentor variabilis* and *Amblyomma americanum*. This form of the disease is found in the South-central and South Atlantic parts of the United States. The second disease form is granulocytic ehrlichiosis (HGE) and is caused by *Ehrlichia equi*. It is hosted and transmitted by the ticks, *Ixodes scapularis, Ixodes pacifica* and *Dermacentor variabilis*. This disease is found throughout the United States. The ticks can also cotransmit Lyme disease. Ehlichiosis is a serious disease since it is associated with some mortality.

The following diseases due to tick-borne pathogens are relatively rarer. Relapsing Fever which is found principally in the western United States is caused by *Borrelia hermsii*. The disease is transmitted by the soft belly tick, *Ornithodoros hermsii*. Colorado Tick Fever (Mountain) is also found in the West and is caused by Colt virus that is hosted by the tick, *Dermacentor Andersen*. Tularemia 35 (Deer Fly Fever or Rabbit Fever) is caused by the microbe, *Francisella tularensis*.

The disease, Tick Paralysis, is caused by a tick-produced toxin and not a microbe. In the West, *Dermacentor Andersen* is the tick involved whereas in the Eastern United States the tick, *Dermacentor variabilis* is involved.

While the United States has a number of different ticks that host various disease related microbial pathogens for humans and animals, similar ticks and tick-borne diseases are found throughout the world including Europe, Africa, Asia, and South America. As an example, while *Ixodes scapularis* and *Ixodes pacificus* serve as vectors for the Lyme disease pathogen, *Borrelia burgdorferi*, in the United States, *Ixodes ricinus* serves as a tick vector in Europe and *Ixodes persulcatus* in Asia.

All ticks of concern in this invention attach to the skin or tissues of mammals, such as humans, either directly through their body parts or initially by the secretion of cement substances that allow them to attach to the host followed by penetration of their mouth parts. The invention provides a method of quickly extricating an embedded tick from the skin thereby preventing or reducing the risk of diseases associated with ticks such as, Lyme disease, Rocky Mountain Spotted Fever and Ehrlichiosis.

Salicylic acid or one of its analogs by virtue of their keratolytic action are employed in the invention to digest and remove dead flaky skin parts and tissues and tick-related cements that have held ticks to the skin of the host. In the cosmetic trade, lotions and ointments are used as scrubs to remove dead skin parts from the surface areas of the body to improve the appearance, beauty and health of the individual. The unexpected finding that a scrubbing lotion could effectively and quickly remove an embedded tick from the skin is the basis of this invention. An exfoliant, e.g., salicylic acid or glycolic acid, is an important element of the compositions described herein. Compositions described herein for the removal of ticks from epidermal tissue may comprise at least one exfoliant in an amount between about 1% and about 35% (glycolic acid, for example), typically in an amount between about 1% and about 25%.

Compositions of this invention comprise an effective amount of salicylic acid or one of its analogs in solutions, lotions, ointments, and soaps to remove embedded ticks from the skin or tissues of human or animal hosts without killing the ticks. An effective concentration of salicylic acid or one of its analogs is typically one to five percent in solutions, lotions, ointments, and soaps and is dependent on the solubility of salicylic acid or one of its analogs, higher amounts are also contemplated. The compositions of the invention whether solutions, lotions, ointments, or soaps are used topically on the skin or tissues to remove embedded ticks from human or animal hosts. Liquid formulations to effect topical delivery of water soluble therapeutic agents are well known in the art, as described in Deckner, et al., U.S. Pat. No. 5,756,118, incorporated herein by reference.

In addition to salicylic acid or analogs thereof, the compositions of the invention can also comprise alcohols such as ethyl alcohol, propyl alcohol, or isopropyl alcohol and alkyl glycols such as ethylene glycol or propylene glycol. In some aspects, the additional agents are useful to effect the solution of salicylic acid or one of its analogs otherwise insoluble and at concentrations that would be ineffective to remove embedded ticks from the skin or tissues of the human or animal host.

In yet a further aspect, a composition of the invention can comprise an astringent used to constrict blood vessels. The astringent may be, for example, Witch Hazel or aluminum salts including, but not limited to, aluminum sulfate, aluminum phosphate and aluminum acetate.

In an exemplary embodiment of the invention, the composition comprises Witch Hazel.

Other exfoliant agents in combination with salicylic acid can be used in the compositions of the invention. For example, glycolic acid can be included along with salicylic acid in the compositions at a concentration/amount similar to that used in other skin compositions known in the art.

In one embodiment, a composition of the invention comprises an aqueous composition of salicylic acid or an analog thereof having between about 0% to about 95% alcohol w/v. Exemplary compositions of the invention comprise between about 2% to about 25% alcohol w/v. Further example compositions of the invention comprise between about 5% to about 20% alcohol w/v or between about 7% to about 17% alcohol, e.g., about 8% w/v. In a specific embodiment, the compositions of the invention comprise between about 9% to about 16% alcohol w/v, e.g., ethanol and/or isopropanol in water.

Moreover, formulations for topical administration of salicylic acid will typically comprise the agent in an amount between about 0.5% to about 10% w/v. Exemplary compositions described herein comprise salicylic acid in an amount between about 1% to about 5% w/v. Compositions typically will comprise salicylic acid for topical administration in an amount between about 1.5% to about 3.5% w/v, e.g., between about 2% to about 3% w/v or between about 1.5% to about 2.5% w/v, for example.

Compositions of the invention can also comprise an effective amount of at least one astringent. Typical astringents as components of formulations described herein include, for example, but are not limited to, Witch Hazel, aluminum sulphate, aluminum phosphate, aluminum acetate and the like, including zinc oxide, and iron oxide. Distilled Witch Hazel is commonly sold in drug stores and pharmacies such as Witch Hazel Mixture 86%, Ethyl Alcohol (CAS #64175) 14%. This common composition is commercially available, for example, from Cumberland Swan One Swan Drive, Smyrna, Tenn. 37167.

Compositions of the invention can also comprise an effective amount of at least one anti-infective agent. Such agents as components of compositions described herein include, but are not limited to, benzalkonium chloride, menthol, neomycin, bacitracin and polymyxin. Anti-infective agents, for example, make up from about 0.1% to about 1% w/v of the compositions described herein.

Commercially available compositions comprising Salicylic acid useful in the methods of the invention are available from Neutrogena, sold under the name NEUTROGENA BLACKHEAD ELIMINATING Daily Scrub Ointment, which contains 2% Salicylic acid, water, cetyl alcohol, PPG15 stearyl ether, polyethylene, Methyl guceth20, steareth21, steareth2, polysorbate60, Glyceryl oleate, coco glucoside, linoleamidopropyl PGdimonium chloride phosphate, Neopentyl glycol dicaprylate/dicaprate, menthol, disodium EDTA, Xanthan gum, potassium cetyl phosphate, agar, mica, titanium dioxide, iron oxide, red 30 lake, and fragrance; and Clinque sold as Clinique Scruffing Lotion 3.5, which contains Witch Hazel, denatured alcohol, water (purified), salicylic acid, butylene glycol, benzalkonium chloride, disodium EDTA copper, disodium EDTA, d & c green No. 5, and fd & c blue No. 1. Clinique also sells Clinique Body Scrub Ointment containing salicylic acid.

The composition(s) of the disclosure can be administered to any host, including a human or nonhuman animal, in an amount effective to inhibit tick biting and/or to cause removal of a tick from a subject. Thus, the compositions are useful as anti-tick agents and may include antiviral agents, and/or antibacterial agents.

Any of a variety of art known methods can be used to administer the compositions to a subject. For example, the compositions of the disclosure can be formulated for topical administration (e.g., as a lotion, cream, spray, gel, or ointment). Examples of formulations in the market place include topical lotions, creams, soaps, wipes, and the like. It may be formulated into liposomes to reduce toxicity or increase bioavailability. Aerosol delivery for transdermal applications may be used. Other methods of administration will be known to those skilled in the art.

Preparations will typically include sterile aqueous or non-aqueous solutions, suspensions, and emulsions. Examples of non-aqueous solvents are propylene glycol, polyethylene glycol, vegetable oils (e.g., olive oil), and organic esters such as ethyl oleate. Examples of aqueous carriers include water, saline, and buffered media, alcoholic/aqueous solutions, and emulsions or suspensions. Preservatives and other additives such as, other antimicrobial, antioxidants, chelating agents, inert gases and the like also can be included.

The disclosure provides a method for inhabiting a tick infection, or a tick-related bacterial or viral associated disease or disorder by contacting or administering a therapeutically effective amount of a composition of the disclosure to a subject who has, or is at risk of having a tick bite, infection or the like. The term "inhibiting" means preventing or ameliorating a sign or symptoms of a tick infection or bite.

The term "therapeutically effective amount" as used herein means an amount of compositions sufficient to remove a tick from a subject's body surface, reduce the risk of a tick bite, and/or reduce the risk of infection by a tick-borne microbe. For example, a therapeutically effective amount can be measured as the amount sufficient to cause a tick to release from a subject or prevent a tick from biting a subject without killing the tick.

If desired, a suitable therapy regime can combine administration of a composition(s) of the disclosure with one or more additional agents, including antiviral and antibacterial agents. The compositions, other therapeutic agents, and/or antibiotic(s) can be administered, simultaneously, but may also be administered sequentially. Suitable antibiotics include aminoglycosides (e.g., gentamicin), betalactams (e.g., penicillins and cephalosporins), quinolones (e.g., ciprofloxacin), and novobiocin. Generally, the antibiotic is administered in a bactericidal amount. However, the peptide provides for a method of increasing antibiotic activity by permeabilizing the bacterial outer membrane and combinations involving peptide and a subinhibitory amount (an amount lower than the bactericidal amount) of antibiotic can be administered. A "bactericidal amount" is an amount sufficient to achieve a bacteria killing blood concentration or bacterial killing local concentration in the subject receiving the treatment. In accordance with its conventional definition, an "antibiotic," as used herein, is a chemical substance that, in dilute solutions, inhibits the growth of, or kills microorganisms. Also encompassed by this term are synthetic antibiotics (e.g., analogs) known in the art.

The invention also provides kits or article of manufacture comprising a composition of the invention and a writing associated the kit or article. The article of manufacture or kit may be, for example, but not limited to a container, bottle or any other means for storing an aqueous solution. The article may be any shape, such as cylindrical, spherical, cubic or conic and any size. The article may be any material suitable for storing the herein described composition such as any plastics, metals or glass.

The writing associated with the article or kit indicates that the composition is useful for removal of ticks. The writing may be for example, but not limited to, instructions for using the herein described composition to remove ticks from a person or animals skin. The instructions may be attached directly to the article or packaged separately with the article.

EXAMPLE I

An embedded wood tick (*Dermacentor variabilis*) in the skin of a human is treated topically with a cotton wipe containing a solution or lotion of 2 percent salicylic acid in aqueous alcohol containing benzalkonium chloride. The tick withdraws from the skin within 20 seconds.

EXAMPLE II

An embedded wood tick (*Dermacentor variabilis*) in the skin within the hair of a dog is treated topically with a cotton wipe saturated with a lotion of 2 percent salicylic acid in aqueous alcohol containing benzalkonium chloride. The tick withdraws from the skin within 30 seconds.

EXAMPLE III

An embedded deer tick (*Ixodes scapularis*) on the skin of a human is treated topically with a cotton wipe containing a lotion of 2 percent salicylic acid an benzalkonium chloride. The tick withdraws from the skin within 20 seconds.

EXAMPLE IV

An embedded deer tick (*Ixodes scapularis*) on the skin of a human is treated topically by applying an ointment containing 5 percent salicylic acid and benzalkonium chloride. the tick withdraws from the skin after 30 seconds.

EXAMPLE V

An embedded Lone Star tick (*Amblyomma americanum*) on the skin of a human is treated topically by applying an ointment containing 5 pecent salicylic acid and benzalkonium chloride. The tick withdraws from the skin within 30 seconds.

EXAMPLE VI

An embedded Lone Star tick (*Amblyomma americanum*) on the skin within the hair of a dog is treated topically with an ointment containing 5 percent salicylic acid and benzalkonium chloride. The tick withdraws from the skin within 30 seconds.

EXAMPLE VII

An embedded deer tick (*Ixodes scapularis*) on the skin within the hair of a dog is treated topically with a cotton wipe saturated with a lotion containing 2 percent salicylic acid and menthol in aqueous alcohol. The tick withdraws from the skin within 30 seconds.

EXAMPLE VIII

An embedded wood tick (*Dermacentor variabilis*) on the skin of a human is treated topically with a cotton wipe containing a lotion of 2 percent salicylic acid and neomycin, bacitracin, and polymyxin in aqueous alcohol. The tick withdraws from the skin within 30 seconds.

EXAMPLE IX

An embedded wood tick (dog tick, *Dermacentor variabilis*) on the skin of a human was treated topically with a cotton swab comprising a lotion of salicylic acid, Witch Hazel, and benzalkonium chloride. It took about 15 seconds for the tick to disengage from the skin.

EXAMPLE X

An embedded wood tick (dog tick, *Dermacentor variabilis*) on the skin within the hair of a dog was treated topically with a cotton swab comprising a lotion of salicylic acid, Witch Hazel, and benzalkonium chloride. It took about 15 seconds for the tick to disengage from the skin.

EXAMPLE XI

An embedded wood tick (dog tick, *Dermacentor variabilis*) on the skin within the hair of a cat was treated topically with a cotton swab comprising a lotion of salicylic acid, Witch Hazel, and benzalkonium chloride. It took about 15 seconds for the tick to disengage from the skin.

With the keratolytic formulations of salicylic acid employed in the invention, embedded ticks are removed by dissolving or otherwise removing the cementitious substances by which they attach themselves to the subject, and with formulations that do not suffocate the thick, the tick emerges alive. Such formulations have a relatively low concentration of salicylic acid (typically about 2%-5%) and include an astringent such as witch hazel. This is in sharp contrast to analgesic formulations which contain much higher concentrations of salicylic acid (typically 10% or more) and kill ticks either by suffocation or by their transdermal properties. The keratolytic formulations are not transdermal and act solely on the surface of the skin.

All publications and patents referred to herein are incorporated by reference.

It is apparent from the foregoing that a new and improved composition and method for removing ticks embedded in the skin and preventing ticks from attaching themselves to and biting humans or other animals have been provided. While only certain presently preferred embodiments have been described in detail, as will be apparent to those familiar with the art, certain changes and modifications can be made without departing from the scope of the invention as defined by the following claims.

The invention claimed is:

1. A method of removing a tick from a subject, comprising the steps of applying a composition containing salicylic acid and an astringent to the tick and/or to the subject near the tick, with the salicylic acid being present in an amount between about 0.5% and 10% w/v of the composition and sufficient to disengage the tick from the subject without killing the tick, and maintaining the composition in contact with the tick and/or the subject until the tick withdraws from the subject.

2. The method of claim 1, wherein the salicylic acid is present in an amount effective to exfoliate a cementitious substance attaching the tick to the subject.

3. The method of claim 1, wherein the astringent is present in an amount effective to constrict blood vessels near the tick and thereby keep blood away from the tick while the tick is being disengaged from the subject.

4. The method of claim 1, wherein the composition also contains an effective amount of at least one anti-infective agent.

5. A method of reducing the risk of tick bites in humans and other mammals comprising the step of contacting the epidermal tissue of a human or other mammal with a composition containing salicylic acid in an amount which is between about 0.5% and 10% w/v of the composition and sufficient to inhibit a tick from cementitiously attaching itself to the tissue without killing the tick.

6. The method of claim 5 wherein the salicylic acid is present in an amount between about 2% w/v and about 5% w/v of the composition.

7. The method of claim 5 wherein the composition also contains an astringent in an amount effective to constrict blood vessels near the skin and thereby keep blood away from the skin where ticks might feed upon it.

8. The method of claim 7 wherein the astringent is witch hazel.

9. The method of claim 8 wherein the witch hazel is present in an amount between about 50% w/v and about 86% w/v of the composition.

10. A method of removing ticks from the skin and reducing the risk of tick bites in humans and other mammals, comprising the step of applying a composition containing an exfoliant selected from the group consisting of salicylic acid, an analog of salicylic acid, glycolic acid, and combinations thereof and at least one astringent to the skin in amounts sufficient to render ineffective cementitious substances secreted by ticks to attach themselves to the skin and to constrict blood vessels near the skin and thereby keep blood away from the skin where ticks might feed upon it, the exfoliant being present in an amount between about 0.5% and 10% w/v of the composition.

11. The method of claim 10 wherein the astringent is witch hazel.

12. The method of claim 11 wherein the salicylic acid is present in an amount between about 2% w/v and about 5% w/v of the composition.

13. The method of claim 10 wherein the composition is applied to the skin near a tick that has already attached itself to the skin.

14. The method of claim 10 wherein the composition is applied to the skin before any ticks have attached themselves to the skin.

15. A method of removing ticks from the skin of humans and other mammals, comprising the step of applying an exfoliant selected from the group consisting of salicylic acid, an analog of salicylic acid, glycolic acid, and combinations thereof to a tick and/or the skin near the tick as part of a composition in which the exfoliant is present in an amount between about 0.5% and 10% w/v of the composition and effective to dissolve any cementitious substance secreted by the tick in attaching itself to the skin without killing the tick, and maintaining the composition in contact with the tick and/or the skin until the tick withdraws from the skin.

16. The method of claim 15 wherein the exfoliant is applied to the skin as part of a composition containing salicylic acid in an amount between about 1% w/v and about 5% w/v, witch hazel in an amount between about 50% w/v and about 86% w/v, and alcohol in an amount between about 8% w/v and about 16% w/v.

* * * * *